US008987187B2

(12) United States Patent
Smets et al.

(10) Patent No.: US 8,987,187 B2
(45) Date of Patent: Mar. 24, 2015

(54) PERFUME SYSTEMS

(75) Inventors: Johan Smets, Lubbeek (BE); Hugo Robert Germain Denutte, Hofstade (Aalst) (BE); An Pintens, Brasschaat (BE); Koen Van Aken, Kuurne (BE); Freek Annie Camiel Vrielynck, Beernem (BE)

(73) Assignee: The Procter & Gamble Company, Cincinnati, OH (US)

( * ) Notice: Subject to any disclaimer, the term of this patent is extended or adjusted under 35 U.S.C. 154(b) by 529 days.

(21) Appl. No.: 13/166,272

(22) Filed: Jun. 22, 2011

(65) Prior Publication Data

US 2011/0308556 A1    Dec. 22, 2011

Related U.S. Application Data

(60) Provisional application No. 61/357,334, filed on Jun. 22, 2010.

(51) Int. Cl.

| | |
|---|---|
| *B08B 3/00* | (2006.01) |
| *A61K 8/84* | (2006.01) |
| *A61K 8/73* | (2006.01) |
| *A61Q 13/00* | (2006.01) |
| *C07C 31/133* | (2006.01) |
| *C07C 33/02* | (2006.01) |
| *C07C 33/14* | (2006.01) |
| *C07C 33/34* | (2006.01) |
| *C07C 43/162* | (2006.01) |
| *C07C 47/21* | (2006.01) |
| *C07C 47/225* | (2006.01) |
| *C07C 47/45* | (2006.01) |
| *C07C 49/11* | (2006.01) |
| *C07C 49/21* | (2006.01) |
| *C07C 49/553* | (2006.01) |
| *C07C 49/792* | (2006.01) |
| *C07C 69/145* | (2006.01) |
| *C07C 255/31* | (2006.01) |
| *C07C 255/46* | (2006.01) |
| *C11B 9/00* | (2006.01) |
| *C11D 3/50* | (2006.01) |
| *A61Q 5/02* | (2006.01) |

(52) U.S. Cl.
CPC . *A61K 8/84* (2013.01); *A61K 8/738* (2013.01); *A61Q 5/02* (2013.01); *A61Q 13/00* (2013.01); *C07C 31/1333* (2013.01); *C07C 33/02* (2013.01); *C07C 33/14* (2013.01); *C07C 33/34* (2013.01); *C07C 43/162* (2013.01); *C07C 47/21* (2013.01); *C07C 47/225* (2013.01); *C07C 47/45* (2013.01); *C07C 49/11* (2013.01); *C07C 49/21* (2013.01); *C07C 49/553* (2013.01); *C07C 49/792* (2013.01); *C07C 69/145* (2013.01); *C07C 255/31* (2013.01); *C07C 255/46* (2013.01); *C07C 2101/02* (2013.01); *C07C 2101/16* (2013.01); *C07C 2102/42* (2013.01); *C11B 9/0015* (2013.01); *C11B 9/0019* (2013.01); *C11B 9/003* (2013.01); *C11B 9/0034* (2013.01); *C11B 9/0046* (2013.01); *C11D 3/50* (2013.01)
USPC ............................................................ 512/1

(58) Field of Classification Search
CPC ........... A61K 8/738; A61K 8/84; C11D 3/50; A61Q 13/00
USPC ............................................................ 512/1
See application file for complete search history.

(56) References Cited

U.S. PATENT DOCUMENTS

| | | | |
|---|---|---|---|
| 3,636,113 A | 1/1972 | Hall | |
| 3,926,859 A | 12/1975 | Lamparsky et al. | |
| 2007/0275866 A1 | 11/2007 | Dykstra | |
| 2010/0137178 A1* | 6/2010 | Smets et al. | 510/104 |
| 2011/0086793 A1 | 4/2011 | Smets et al. | |

FOREIGN PATENT DOCUMENTS

| | | | | |
|---|---|---|---|---|
| CH | 572 340 A5 | | 2/1976 | |
| JP | S50-93957 | * | 7/1975 | .............. C07C 47/38 |
| PL | 128 581 | * | 4/1985 | .............. C07C 33/05 |

OTHER PUBLICATIONS

English Translation of JP50-093957 by the McElroy Translation Company. Jan. 2014.*
Machine Translation of PL 128 581. Obtained May 9, 2014 at https://translate.google.com/.*
Iwasa, et al., Tandem Radical Cyclization of Acyclic Homoallylic Xanthates: Cyclopentannulated γ-Thionolactone and γ-Lactones, J. Org. Chem., Apr. 1, 1991, pp. 2849-2853, vol. 56, No. 8.
International Search Report, International Application No. PCT/US2011/041387, date of mailing Dec. 8, 2011, 6 pages.
U.S. Appl. No. 13/166,263, filed Jun. 22, 2011, Smets, et al.

* cited by examiner

*Primary Examiner* — Ling Choi
*Assistant Examiner* — Lanee Reuther
(74) *Attorney, Agent, or Firm* — James F. McBride; Steven W. Miller

(57) ABSTRACT

The present application relates to perfume raw materials, perfume delivery systems and consumer products comprising such perfume raw materials and/or such perfume delivery systems, as well as processes for making and using such perfume raw materials, perfume delivery systems and consumer products. Such perfume raw materials and compositions, including the delivery systems, disclosed herein expand the perfume communities' options as such perfume raw materials can provide variations on character and such compositions can provide desired odor profiles.

15 Claims, No Drawings

PERFUME SYSTEMS

CROSS REFERENCE TO RELATED APPLICATIONS

This application claims priority under 35 U.S.C. §119(e) to U.S. Provisional Application Ser. No. 61/357,334 filed Jun. 22, 2010.

FIELD OF INVENTION

The present application relates to perfume raw materials, perfume delivery systems and consumer products comprising such perfume raw materials and/or such perfume delivery systems, as well as processes for making and using such perfume raw materials, perfume delivery systems and consumer products.

BACKGROUND OF THE INVENTION

Consumer products may comprise one or more perfumes and/or perfume delivery systems that can provide a desired scent to such product and/or a situs that is contacted with such a product and/or mask an undesirable odor. While current perfumes and perfume delivery systems provide desirable odors, consumers continue to seek products that have scents that may be longer lasting and that are tailored to their individual desires (see for example USPA 2007/0275866 A1 and U.S. patent application Ser. No. 12/133,866)—unfortunately the pool of perfume raw materials and perfume delivery systems that is available is still too limited to completely meet the perfume community's needs. Thus, perfumers need an ever larger pool of perfume raw materials and perfume delivery systems.

Applicants believe that the perfume raw materials and compositions, including the delivery systems, disclosed herein expand the perfume community's options, as such perfume raw materials can provide variations on character and such compositions can provide desired odor profiles. In certain aspects, such perfume raw materials and/or perfume delivery systems comprising such perfume raw materials provide variations on character and/or odor profiles that are better than expected as measured by parameters such as headspace analysis which can be used to determine perfume delivery system perfume leakage and/or perfume delivery efficiency; Clog P; boiling point and/or odor detection threshold.

SUMMARY OF THE INVENTION

The present application relates to perfume raw materials, perfume systems and consumer products comprising such perfume raw materials and/or such perfume delivery systems, as well as processes for making and using such perfume raw materials, perfume systems and consumer products.

DETAILED DESCRIPTION OF THE INVENTION

Definitions

As used herein "consumer product" means baby care, beauty care, fabric & home care, family care, feminine care, health care, snack and/or beverage products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshing that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Perfumes and Consumer Products Comprising Same

In one aspect, a perfume comprising an optional solvent and a perfume raw material selected from the group consisting of:

a) a perfume raw material having the following structure:

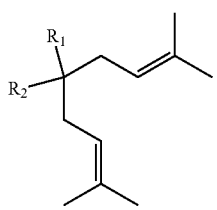

Formula 1 wherein $R_1$ is selected from the group consisting of:
(i) CHO
(ii) $CR_3R_4OR_5$ wherein $R_3$, $R_4$ and $R_5$ are each independently selected from a group consisting of hydrogen, a straight or branched $C_1$-$C_5$ alkyl moiety, a straight or branched $C_2$-$C_5$ alkenyl moiety, a straight or branched $C_2$-$C_5$ alkyl moiety comprising a ketone moiety, and a straight or branched $C_2$-$C_5$ alkenyl moiety comprising a ketone moiety;

wherein $R_2$ is selected from the group consisting of:
(i) hydrogen;
(ii) a straight or branched $C_1$-$C_6$ alkyl moiety;
(iii) a straight or branched $C_2$-$C_6$ alkenyl moiety; and
(iv) a straight or branched $C_2$-$C_6$ alkyne moiety;

b) a perfume raw material having the following structure:

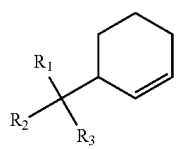

Formula 2 wherein $R_1$ is selected from the group consisting of
(i) CHO
(ii) $CR_4R_5OR_6$ wherein $R_4$, $R_5$ and $R_6$ are each independently selected from a group consisting of hydrogen, a straight or branched $C_1$-$C_5$ alkyl moiety, a straight or branched $C_2$-$C_5$ alkenyl moiety, a straight or branched $C_2$-$C_5$ alkyl moiety comprising a ketone moiety, and a straight or branched $C_2$-$C_5$ alkenyl moiety comprising a ketone moiety;

wherein $R_2$ and $R_3$ are each independently selected from a group consisting of
(i) a straight or branched $C_1$-$C_6$ alkyl moiety;
(ii) a straight or branched $C_2$-$C_6$ alkenyl moiety;

in one aspect, when $R_2$ and $R_3$ are taken together, $R_2$ and $R_3$, form a ring structure, in one aspect, a $C_3$-$C_6$ ring structure, in one aspect, said ring structure is selected from cyclopropane, cyclobutane, cyclopentane, or cyclohexane;

c) a perfume raw material having the following structure:

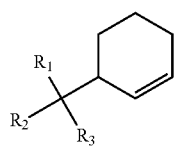

Formula 3 wherein $R_1$ is selected from the group consisting of:
(i) a nitrile moiety;
(ii) C=OR where R is selected from the group consisting of hydrogen, a straight or branched $C_1$-$C_5$ alkyl moiety, a straight or branched $C_2$-$C_5$ alkenyl moiety, and $R_2$ and $R_3$, form a ring structure selected from cyclopropane, cyclobutane, cyclopentane, or cyclohexane, in another aspect, $R_1$ is methylketone, and $R_2$ and $R_3$ are each methyl.

d) a perfume raw material having the following structure:

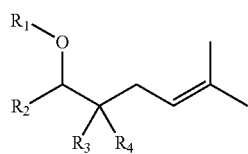

Formula 4 wherein $R_1$ is selected from the group consisting of:
  (i) a straight or branched $C_1$-$C_6$ alkyl moiety;
  (ii) a straight or branched $C_2$-$C_6$ alkenyl moiety;
  (iii) a straight or branched $C_2$-$C_6$ alkyne moiety;
  (iv) $COR_5$ where $R_5$ is selected from the group consisting of a straight or branched $C_1$-$C_5$ alkyl moiety, a straight or branched $C_2$-$C_5$ alkenyl moiety;
  (v) $COOR_5$ where $R_5$ is selected from a group consisting of a straight or branched $C_1$-$C_5$ alkyl moiety, a straight or branched $C_2$-$C_5$ alkenyl moiety;
wherein $R_2$ is selected from the group consisting of:
  (i) hydrogen;
  (ii) a straight or branched $C_1$-$C_6$ alkyl moiety;
  (iii) a straight or branched $C_2$-$C_4$ alkenyl moiety; and
  (iv) a straight or branched $C_2$-$C_6$ alkyne moiety;
wherein $R_3$ and $R_4$ are each independently selected from a group consisting of:
  (i) a straight or branched $C_1$-$C_6$ alkyl moiety;
  (ii) a straight or branched $C_2$-$C_4$ alkenyl moiety;
  (iii) a straight or branched $C_2$-$C_6$ alkyne moiety; or
  in one aspect when $R_3$ and $R_4$ are taken together, $R_3$ and $R_4$ form a ring structure, in one aspect, a $C_3$-$C_6$ ring structure, in one aspect, said ring structure is selected from cyclopropane, cyclobutane, cyclopentane, or cyclohexane;
e) a perfume raw material having the following structure:

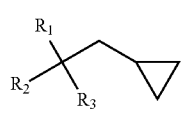

Formula 5 wherein $R_1$ is selected from the group consisting of:
  (i) CHO;
  (ii) CN;
  (iii) $COR_4$
    wherein $R_4$ is selected from the group consisting of a straight or branched $C_1$-$C_6$ alkyl moiety; a straight or branched $C_2$-$C_6$ alkenyl moiety; a straight or branched $C_2$-$C_6$ alkyne moiety; a non-substituted phenyl moiety; a substituted phenyl moiety, in one aspect, said substituted phenyl moiety may comprise a substitutent selected from methyl and/or ethyl;
  (iv) $CR_5R_6OR_7$ wherein $R_5$, $R_6$ and $R_7$ are each independently selected from a group consisting of hydrogen, a straight or branched $C_1$-$C_5$ alkyl moiety, a straight or branched $C_2$-$C_5$ alkenyl moiety, a straight or branched $C_2$-$C_5$ alkyl moiety comprising a ketone moiety, and a straight or branched $C_2$-$C_5$ alkenyl moiety comprising a ketone moiety;
  (v) $COOR_8$ where $R_8$ is selected from a group consisting of a straight or branched $C_1$-$C_5$ alkyl moiety, a straight or branched $C_2$-$C_5$ alkenyl moiety;
wherein $R_2$ is selected from the group consisting of:
  (i) a straight or branched $C_1$-$C_6$ alkyl moiety;
  (ii) a straight or branched $C_2$-$C_6$ alkenyl moiety;
  (iii) a straight or branched $C_2$-$C_6$ alkyne moiety; and
  (iv) $CH_2$-cyclopropyl
wherein $R_3$ is selected from the group consisting of:
  (i) a straight or branched $C_1$-$C_6$ alkyl moiety;
  (ii) a straight or branched $C_2$-$C_6$ alkenyl moiety;
  (iii) a straight or branched $C_2$-$C_6$ alkyne moiety; and
  in one aspect, when $R_2$ and $R_3$ are taken togther, $R_2$ and $R_3$ form a ring structure, in one aspect, a $C_3$-$C_6$ ring structure, in one aspect, said ring structure is selected from cyclopropane, cyclobutane, cyclopentane, or cyclohexane;
f) a perfume raw material having the following structure:

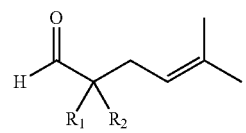

Formula 6 wherein $R_1$ and $R_2$ are each independently selected from the group consisting of:
  (i) a straight or branched $C_1$-$C_6$ alkyl moiety;
  (ii) a straight or branched $C_2$-$C_4$ alkenyl moiety;
  (iii) a straight or branched $C_2$-$C_6$ alkyne moiety; and
  in one aspect, when $R_1$ and $R_2$ are taken togther, $R_1$ and $R_2$ form a ring structure, in one aspect, a $C_3$-$C_6$ ring structure, in one aspect, said ring structure is selected from cyclopropane, cyclobutane, cyclopentane, or cyclohexane;
g) a perfume raw material having the following structure:

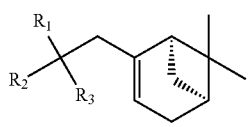

Formula 7 wherein $R_1$ is selected from the group consisting of:
  (i) CHO;
  (ii) a nitrile moiety;
  (iii) $COR_4$
    wherein $R_4$ is selected from the group consisting of a straight or branched $C_1$-$C_6$ alkyl moiety; a straight or branched $C_2$-$C_6$ alkenyl moiety; a straight or branched $C_2$-$C_6$ alkyne moiety; a non-substituted phenyl moiety; a substituted phenyl moiety, in one aspect, said substituted phenyl moiety may comprise a substitutent selected from methyl and/or ethyl;
  (iv) $CR_5R_6OR_7$ wherein $R_5$, $R_6$ and $R_7$ are each independently selected from a group consisting of hydrogen, a straight or branched $C_1$-$C_5$ alkyl moiety, a straight or branched $C_2$-$C_5$ alkenyl moiety, a straight or branched $C_2$-$C_5$ alkyl moiety comprising a ketone moiety, and a straight or branched $C_2$-$C_5$ alkenyl moiety comprising a ketone moiety;
  (v) $COOR_8$ where $R_8$ is selected from a group consisting of a straight or branched $C_1$-$C_5$ alkyl moiety, a straight or branched $C_2$-$C_5$ alkenyl moiety;

wherein $R_2$ is selected from the group consisting of:
(i) a straight or branched $C_1$-$C_6$ alkyl moiety;
(ii) a straight or branched $C_2$-$C_6$ alkenyl moiety;
(iii) a straight or branched $C_2$-$C_6$ alkyne moiety; and
(iv) $CH_2$-cyclopropyl wherein $R_3$ is selected from the group consisting of:
(i) a straight or branched $C_1$-$C_6$ alkyl moiety;
(ii) a straight or branched $C_2$-$C_6$ alkenyl moiety;
(iii) a straight or branched $C_2$-$C_6$ alkyne moiety; and
in one aspect, when $R_2$ and $R_3$ are taken togther, $R_2$ and $R_3$ form a ring structure, in one aspect, a $C_3$-$C_6$ ring structure, in one aspect, said ring structure is selected from cyclopropane, cyclobutane, cyclopentane, or cyclohexane is disclosed.

In one aspect, the aforementioned perfume may comprise, based on total perfume weight, from about 0.0001% to about 50%, or even from about 0.01% to about 25% of one or more of said perfume raw materials.

In addition to the aforementioned perfume, A consumer product comprising said perfume and an adjunct ingredient is disclosed.

In one aspect, said consumer product may be a cleaning and/or treatment composition and comprising an adjunct ingredient.

In one aspect, said consumer product may be a fabric and/or hard surface cleaning and/or treatment composition, that may comprise, based on total composition weight, from about 0.00001% to about 35%, or from about 0.01% to about 25% of said perfume.

In one aspect, said consumer product may be a detergent that may comprise, based on total detergent weight, from about 0.00001% to about 35%, or from about 0.01% to about 25% of said perfume.

In one aspect, said consumer product may be a highly compacted consumer product, said highly compacted consumer product may comprise based on total highly compacted consumer product weight, from about 0.00001% to about 35%, or from about 0.01% to about 25% of said perfume.

Examples of perfume raw materials that have the structure of Formula 1 are Table 1 Materials 1, 2 and 3.

Examples of perfume raw materials that have the structure of Formula 2 are Table 1 Materials 4, 5, 6, 7, 8 and 9.

Examples of perfume raw materials that have the structure of Formula 3 are Table 1 Materials 10, 11, 12 and 13.

Examples of perfume raw materials that have the structure of Formula 4 are Table 1 Materials 14, 15, 16, 17, 18, 19 and 20.

Examples of perfume raw materials that have the structure of Formula 5 are Table 1 Materials 21, 22, 23, 24 and 25.

An example of a perfume raw material that has the structure of Formula 6 is Table 1 Material 26.

Examples of perfume raw materials that have the structure of Formula 7 are Table 1 Materials 27, 28, 29 and 30.

TABLE 1

Suitable Perfume Raw Materials (herein after "PRMs")
Suitable PRMs include the PRMs listed in Table 1 below and stereoisomers thereof.

| | Chemical structure | IUPAC Names | Molecules Characteristics |
|---|---|---|---|
| 1 | 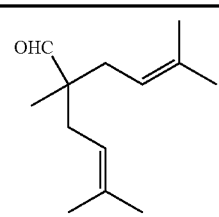 | 2,5-dimethyl-2-(3-methylbut-2-enyl)hex-4-enal | green, citrus, very fresh |
| 2 | 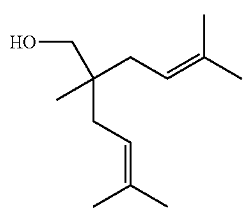 | 2,5-dimethyl-2-(3-methylbut-2-enyl)hex-4-en-1-ol | lime, terpineol, marseille soap |
| 3 | 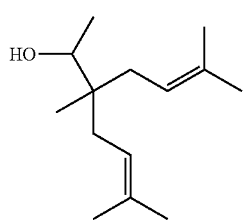 | 3,6-dimethyl-3-(3-methylbut-2-enyl)hept-5-en-2-(R,S)-ol | floral, citrus |
| 4 | 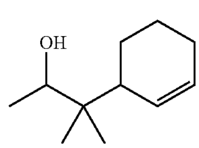 | 3-(cyclohex-2-enyl)-3-methylbutan-2-(R,S)-ol | lilac, lime |

TABLE 1-continued

Suitable Perfume Raw Materials (herein after "PRMs")
Suitable PRMs include the PRMs listed in Table 1
below and stereoisomers thereof.

| | Chemical structure | IUPAC Names | Molecules Characteristics |
|---|---|---|---|
| 5 | 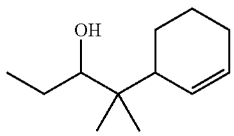 | 2-(cyclohex-2-enyl)-2-methylpentan-3-(R,S)-ol | herbal, woody (patchouli) |
| 6 | 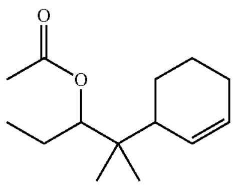 [SMILES: CCC(OC(C)=O)C(C)(C)C1C=CCCC1] | 2-(cyclohex-2-enyl)-2-methylpentan-3-(R,S)-yl acetate | woody, fruity |
| 7 | 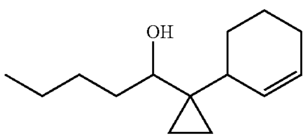 | 1-(1-(cyclohex-2-enyl)-cyclopropyl)pentan-1-(R,S)-ol | green (dark green) |
| 8 | 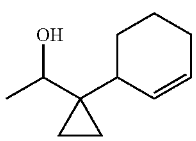 | 1-(R,S)-(1-(cyclohex-2-enyl)cyclopropyl)ethanol | floral (rose, violet) |
| 9 | 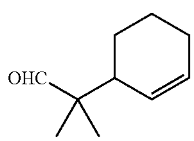 | 2-(cyclohex-2-enyl)-2-methylpropanal | intense, ozonic, floral, green |
| 10 | 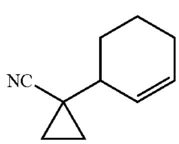 [SMILES: N#CC1(C2C=CCCC2)CC1] | 1-(cyclohex-2-enyl)cyclopropanecarbonitrile | aromatic, spicy, woody |
| 11 | 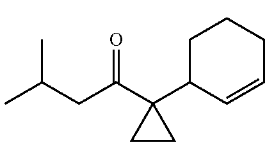 | 1-(1-(cyclohex-2-enyl)cyclopropyl)-3-methylbutan-1-one | floral, fruity |
| 12 | 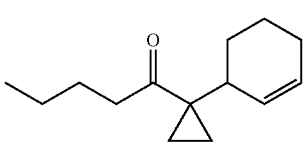 | 1-(1-(cyclohex-2-enyl)cyclopropyl)pentan-1-one | metallic, green |
| 13 | 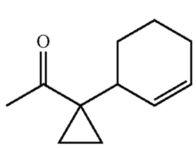 | 1-(1-(cyclohex-2-enyl)cyclopropyl)ethanone | indolic/dipentene-animalic |

TABLE 1-continued

Suitable Perfume Raw Materials (herein after "PRMs")
Suitable PRMs include the PRMs listed in Table 1
below and stereoisomers thereof.

| | Chemical structure | IUPAC Names | Molecules Characteristics |
|---|---|---|---|
| 14 | 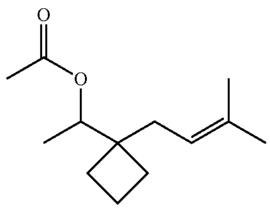 | 1-(R,S)-(1-(3-methylbut-2-enyl)cyclobutyl)ethyl acetate | herbal, floral |
| 15 | 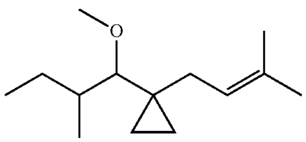 | 1-(1-(R,S)-methoxy-2-(R,S)-methylbutyl)-1-(3-methylbut-2-enyl)cyclopropane | rose, clean linen |
| 16 | 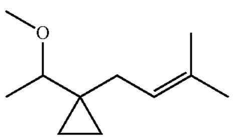 | 1-(1-(R,S)-methoxyethyl)-1-(3-methylbut-2-enyl)cyclopropane | fresh, floral (jasmin) |
| 17 | 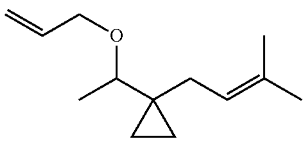 | 1-(1-(R,S)-(allyloxy)ethyl)-1-(3-methylbut-2-enyl)cyclopropane | aromatic, spicy |
| 18 | 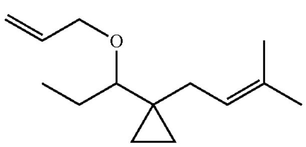 | 1-(1-(R,S)-(allyloxy)propyl)-1-(3-methylbut-2-enyl)cyclopropane | aromatic, spicy |
| 19 | 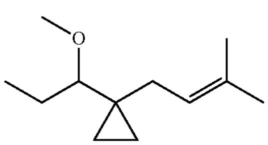 | 1-(1-(R,S)-methoxypropyl)-1-(3-methylbut-2-enyl)cyclopropane | fruity, citrus, fresh |
| 20 | 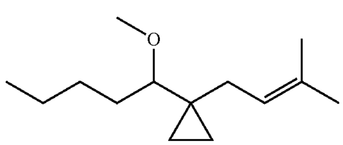 | 1-(1-(R,S)-methoxypentyl)-1-(3-methylbut-2-enyl)cyclopropane | aromatic, citrus |
| 21 | 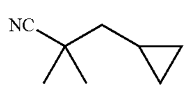 | 3-cyclopropyl-2,2-dimethylpropanenitrile | spicey, mint, camphor |
| 22 | 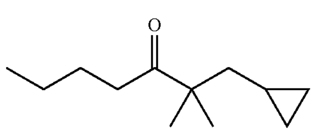 | 1-cyclopropyl-2,2-dimethylheptan-3-one | floral, herbal |
| 23 | 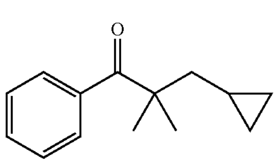 | 3-cyclopropyl-2,2-dimethyl-1-phenylpropan-1-one | woody, floral (violet), thymol |

TABLE 1-continued

Suitable Perfume Raw Materials (herein after "PRMs")
Suitable PRMs include the PRMs listed in Table 1
below and stereoisomers thereof.

| | Chemical structure | IUPAC Names | Molecules Characteristics |
|---|---|---|---|
| 24 | 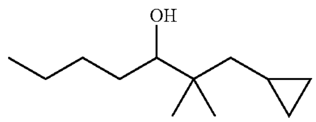 | 1-cyclopropyl-2,2-dimethylheptan-3-(R,S)-ol | woody, earthy, hay |
| 25 | 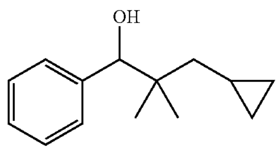 | 3-cyclopropyl-2,2-dimethyl-1-phenylpropan-1-(R,S)-ol | Woody |
| 26 | 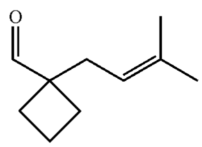 | 1-(3-methylbut-2-enyl)cyclobutanecarbaldehyde | green (bambou), floral |
| 27 | 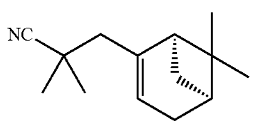 | 3-((1R,5S)-6,6-dimethylbicyclo[3.1.1]hept-2-en-2-yl)-2,2-dimethylpropanenitrile | woody, violet, cedarwood |
| 28 | 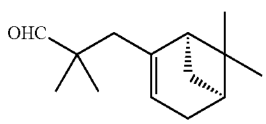 | 3-((1R,5S)-6,6-dimethylbicyclo[3.1.1]hept-2-en-2-yl)-2,2-dimethylpropanal | aldehydic, floral (ozonic), woody |
| 29 | 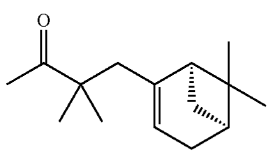 [SMILES: CC(=O)C(C)(C)CC1=CC[C@H]2C[C@@H]1C2(C)C] | 4-((1R,5S)-6,6-dimethylbicyclo[3.1.1]hept-2-en-2-yl)-3,3-dimethylbutan-2-one | cedarwood |
| 30 | 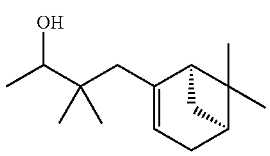 [SMILES: CC(O)C(C)(C)CC1=CC[C@H]2C[C@@H]1C2(C)C] | 4-((1R,5S)-6,6-dimethyl-bicyclo[3.1.1]hept-2-en-2-yl)-3,3-dimethylbutan-2-(R,S)-ol | woody |

The PRMs disclosed in herein via structures/Formula and the specific PRMs of Table 1 above may provide one or more of the following benefits at a level that Applicants believe is unexpected in view of PRMs in general: neat product odor; wet fabric odor when applied to a fabric; dry fabric odor when applied to a fabric; reduced leakage from an encapsulate, including an encapsulate such as a perfume microcapsule; increased head space versus neat oil in certain perfume delivery technologies; odor when used in a matrix perfume delivery that is applied to a package; neat product odor when applied to a cleaning and/or treatment composition; fine fragrance composition odor when used in a fine fragrance; dry hair odor when a composition comprising such a PRM is applied to hair; PRM bloom from a solution comprising such a PRM and new PRM character when applied to a situs. Confirmation of such benefits can be obtained by applying standard test methodologies.

The PRMs and stereoisomers of such PRMs (also known as molecules in the examples of the present specification) disclosed in Table 1 above can be made in accordance with the respective teachings found, for example in the examples of the present specification.

Perfume Delivery Systems and Consumer Products Comprising Same

In one aspect, a perfume delivery system that may comprise, based on total delivery system weight, from about from about 0.001% to about 99%, 0.1% to about 90%, or from about 1% to about 75%, of said perfume is disclosed.

In one aspect, said perfume delivery system may be a polymer assisted delivery system; molecule-assisted delivery system; fiber-assisted delivery system; amine assisted delivery system; cyclodextrin delivery system; starch encapsulated accord; inorganic carrier delivery system; or pro-perfume.

In one aspect, said perfume delivery system may be a nanocapsule or microcapsule comprising, based on total nanocapsule or microcapsule weight, from about 0.001% to about 99%, from about 0.1% to about 95% or from about 0.1% to about 87% of said perfume.

In one aspect, said perfume delivery system may be a starch encapsulated accord.

In one aspect, said perfume delivery system may be a cyclodextrin delivery system that may comprise, based on total perfume delivery system weight from about 2% to about 20%, from about 3% to about 10% or from about 5% to about 8% of said perfume.

In one aspect, said perfume delivery system may be a polymer assisted delivery matrix system comprising.

In one aspect, said perfume delivery system may be an amine assisted delivery system.

In one aspect, said perfume delivery system may be a pro-perfume amine reaction product.

In one aspect, a consumer product that may comprise, based on total consumer product weight, from about 0.001% to about 20% of any perfume delivery system or combination of said perfume delivery systems disclosed herein is disclosed.

In one aspect, said consumer product may comprise said delivery system and one or more of the perfumes disclosed herein.

Perfume Delivery System Details

Certain perfume delivery systems, methods of making certain perfume delivery systems and the uses of such perfume delivery systems are disclosed in USPA 2007/0275866 A1. Such perfume delivery systems include:

I. Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable micro-particles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccarides and nanolatexes may be combined with other PDTs, including other PAD systems such as PAD reservoir systems in the form of a perfume microcapsule (PMC). Polymer Assisted Delivery (PAD) matrix systems may include those described in the following references: U.S. Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in WO 2005/102261; USPA 20050124530A1; USPA 20050143282A1; and WO 2003/015736. Functionalized silicones may also be used as described in USPA 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in U.S. Pat. No. 4,911,852; USPA 2004/0058845 A1; USPA 2004/0092425 A1 and USPA 2005/0003980 A1.

b.) Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD. Perfume microcapsules (PMC) may include those described in the following references: U.S. Patent Applications: 2003/0125222 A1; 2003/215417 A1; 2003/216488 A1; 2003/158344 A1; 2003/165692 A1; 2004/071742 A1; 2004/071746 A1; 2004/072719 A1; 2004/072720 A1; 2006/0039934 A1; 2003/203829 A1; 2003/195133 A1; 2004/087477 A1; 2004/0106536 A1; and U.S. Pat. Nos. 6,645,479 B1; 6,200,949 B1; 4,882,220; 4,917,920; 4,514,461; 6,106,875 and 4,234,627, 3,594,328 and U.S. RE 32,713.

II. Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2. Molecule-Assisted Delivery (MAD) may also include those described in U.S. Pat. No. 7,119,060 and U.S. Pat. No. 5,506,201.

III. Fiber-Assisted Delivery (FAD): The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermomechanical pulp and bleached or unbleached kraft or sulfite pulps. Animal fibers consist largely of particular proteins, such as silk, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one aspect, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

IV. Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines. Without technology, volatile top notes can be lost too quickly, leaving a higher ratio of middle and base notes to top notes. The use of a polymeric amine allows higher levels of top notes and other PRMS to be used to obtain freshness longevity without causing neat product odor to be more intense than desired, or allows top notes and other PRMs to be used more efficiently. In one aspect, AAD systems are effective at delivering PRMs at pH greater than about neutral. Without wishing to be bound by theory, conditions in which more of the amines of the AAD system are deprotonated may result in an increased affinity of the deprotonated amines for PRMs such as aldehydes and ketones, including unsaturated ketones and enones such as damascone. In another aspect, polymeric amines are effective at delivering PRMs at pH less than about neutral. Without wishing to be bound by theory, conditions in which more of the amines of the AAD system are protonated may result in a decreased affinity of the protonated amines for PRMs such as aldehydes and ketones, and a strong affinity of the polymer framework for a broad range of PRMs. In such an aspect, polymer-assisted delivery may be delivering more of the perfume benefit; such systems are a subspecies of AAD and may be referred to as Amine-Polymer-Assisted Delivery or APAD. In some cases when the APAD is employed in a composition that has a pH of less than seven, such APAD systems may also be considered Polymer-Assisted Delivery (PAD). In yet another aspect, AAD and PAD systems may interact with other materials, such as anionic surfactants or polymers to form coacervate and/or coacervates-like systems. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. Suitable AAD systems as well as methods of making same may be found in U.S. Patent Applications 2005/0003980 A1; 2003/0199422 A1; 2003/0036489 A1; 2004/0220074 A1 and U.S. Pat. No. 6,103,678.

V. Cyclodextrin Delivery System (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2005/0003980 A1 and 2006/0263313 A1 and U.S. Pat. Nos. 5,552,378; 3,812,011; 4,317,881; 4,418,144 and 4,378,923.

VI. Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in USPA 2005/0003980 A1 and U.S. Pat. No. 6,458,754 B1.

VII. Inorganic Carrier Delivery System (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1 and U.S. Pat. Nos. 5,858,959; 6,245,732 B1; 6,048,830 and 4,539,135. Silica is another form of ZIC. Another example of a suitable inorganic carrier includes inorganic tubules, where the perfume or other active material is contained within the lumen of the nano- or micro-tubules. In one aspect, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

VIII. Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may be pre-formed or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiff bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester. The typical trigger for perfume release is exposure to water; although other triggers may include enzymes, heat, light, pH change, autoxidation, a shift of equilibrium, change in concentration or ionic strength and others. For aqueous-based products, light-triggered pro-perfumes are particularly suited. Such photo-pro-perfumes (PPPs) include but are not limited to those that release coumarin derivatives and perfumes and/or pro-perfumes upon being triggered. The released pro-perfume may release one or more PRMs by means of any of the above mentioned triggers. In one aspect, the photo-pro-perfume releases a nitrogen-based pro-perfume when exposed to a light and/or moisture trigger. In another aspect, the nitrogen-based pro-perfume, released from the photo-pro-perfume, releases one or more PRMs selected, for example, from aldehydes, ketones (including enones) and alcohols. In still another aspect, the PPP releases a dihydroxy coumarin derivative. The light-triggered pro-perfume may also be an ester that releases a coumarin derivative and a perfume alcohol. In one aspect the pro-perfume is a dimethoxybenzoin derivative as described in USPA 2006/0020459 A1. In another aspect the pro-perfume is a 3', 5'-dimethoxybenzoin (DMB) derivative that releases an alcohol upon exposure to electromagnetic radiation. In yet another aspect, the pro-perfume releases one or more low ODT PRMs, including tertiary alcohols such as linalool, tetrahydrolinalool, or dihydromyrcenol. Suitable pro-perfumes and methods of making same can be found in U.S. Pat. Nos. 7,018,978 B2; 6,987,084 B2; 6,956,013 B2; 6,861,402 B1; 6,544,945 B1; 6,093,691; 6,277,796 B1; 6,165,953; 6,316,397 B1; 6,437,150 B1; 6,479,682 B1; 6,096,918; 6,218,355 B1; 6,133,228; 6,147,037; 7,109,153 B2; 7,071,151 B2; 6,987,084 B2; 6,610,646 B2 and 5,958,870, as well as can be found in USPA 2005/0003980 A1 and USPA 2006/0223726 A1.

a.) Amine Reaction Product (ARP): For purposes of the present application, ARP is a subclass or species of PP. One may also use "reactive" polymeric amines in which the amine functionality is pre-reacted with one or more PRMs to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Adjunct Materials

For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

Each adjunct ingredient is not essential to Applicants' compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Method of Use

Certain of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application should be used to determine the respective values of the parameters of Applicants' invention as such invention is described and claimed herein.

(1) Clog P

The "calculated log P" (Clog P) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). Clog P values may be calculated by using the "CLOGP" program available from Daylight Chemical Information Systems Inc. of Irvine, Calif. U.S.A.

(2) Boiling Point

Boiling point is measured by ASTM method D2887-04a, "Standard Test Method for Boiling Range Distribution of Petroleum Fractions by Gas Chromatography," ASTM International.

(3) Headspace Ratio (a) Obtain a fragrance free consumer product formulation (shampoo or leave-on conditioner).

(b) Obtain fragrance microcapsules whose water content has been adjusted to achieve a perfume content of 25 wt % in the aqueous slurry.

(c) Prepare Sample A by adding 2.0 grams of the fragrance microcapsule aqueous slurry to 95 grams of the fragrance free consumer product formulation. Then add 3.0 grams of deionized water to balance the formulation to 100 grams. Age this formulation for 1 week at 40 degrees Centigrade.

(d) Prepare Sample B by adding 0.50 grams of the neat fragrance to 95 grams of fragrance free consumer product formulation. Then add 4.5 grams of deionized water to balance the formulation to 100 grams. Age this formulation for 1 week at 40 degrees Centigrade.

The Headspace Ratio for determining perfume leakage from a perfume delivery system is defined as the headspace concentration of Sample A divided by the headspace concentration of Sample B, $$\frac{H_{Sample\_A}}{H_{Sample\_B}},$$

where $H_{Sample\_A}$ is the headspace concentration of a consumer product formulation Sample A, and $H_{Sample\_B}$ is the headspace concentration of a consumer product formulation Sample B.

The Headspace Ratio for determining perfume delivery efficiency from a perfume delivery system is defined as the headspace concentration of Sample B divided by the headspace concentration of Sample A, $$\frac{H_{Sample\_B}}{H_{Sample\_A}},$$

where $H_{Sample\_A}$ is the headspace concentration of a consumer product formulation Sample A, and $H_{Sample\_B}$ is the headspace concentration of a consumer product formulation Sample B.

Solid-Phase Micro-Extraction (SPME)-Gas Chromatography/Mass Spectrometry is used to measure the level of perfume raw materials in the headspace of products. 1.0 grams of the 1 week at 40 degrees Centigrade aged sample (shampoo or conditioner) are placed into a clean 20 ml headspace vial and allowed to equilibrate for at least 2 hours at room temperature.

The samples are then analyzed using the MPS2-SMPE-GC-MS analysis system (GC-02001-0153, MSD-02001-0154, MPS2-02001-0155).

Apparatus:
1. 20 ml headspace vial
2. Timer.
3. Gas Chromatograph (GC): Agilent model 6890 with a CIS-4 injector (Gerstel, Mulheim, Germany) and MPS-2 Autosampler and TDU. For SPME analysis, we used the split/splitless injector (not the CIS-4 injector).
4. GC column: J&W DB-5 MS, 30 M×0.25 mm ID, 1.0 m film thickness obtained from J&W Scientific of Folsom, Calif., USA.
5. Carrier gas, helium, 1.5 ml/min. flow rate.
6. The injector liner is a special SPME liner (0.75 mm ID) from Supelco.
7. The Detector is a model 5973 Mass Selective Detector obtained from Agilent Technologies, Inc., Wilmington, Del., USA having a source temperature of about 230° C., and a MS Quad temperature of about 150° C.

Analysis Procedure:
1. Transfer sample to proper sample tray and proceed with SPME-GC-MS analysis.
2. Start sequence of sample loading and analysis. In this step, the sample is allowed to equilibrate for at least two hours on the auto sampler tray, then sampled directly from the tray. The SPME fiber assembly is DVB/CAR/PDMS (50/30 um, 24 ga, 1 cm length). Sampling time is 5 minutes.
3. Injector temperature is at 260 C.
4. Then GC-MS analysis run is started. Desportion time is 5 minutes.
5. The following temperature program is used:
    i) an initial temperature of about 50° C. which is held for 3 minutes,
    ii) increase the initial temperature at a rate of about 6° C./min until a temperature of about 250° C. is reached, then 25° C./min to 275° C., hold at about 275° C. for 4.67 minute.
6. Perfume compounds are identified using the MS spectral libraries of John Wiley & Sons and the National Institute of Standards and Technology (NIST), purchased and licensed through Hewlett Packard.
7. Chromatographic peaks for specific ions are integrated using the Chemstation software obtained from Agilent Technologies, Inc., Wilmington, Del., USA.
8. The ratio for each PRM is calculated by dividing the peak area for the perfume raw material in Sample A by the peak area in Sample B.
9. Each ratio is then weighted by that perfume raw material's weight composition in the perfume.
10. The Headspace Ratio is calculated as the sum of the individual perfume raw material ratios obtained in step 9.

(4) Perfume Leakage can Also be Evaluated Via % Liquid-Liquid Extraction and Gas Chromatographic-Mass Spectrometric Analysis When determining the % perfume leakage from Perfume Microcapsules in liquid detergent, a fresh sample of liquid detergent with equal level of free perfume (without Perfume Microcapsules) must also be analysed in parallel for reference.

1. Preparation of an Internal Standard Solution
    Stock solution of tonalid: Weigh 70 mg tonalid and add 20 ml hexane p.a.
    Internal Standard Solution solution: Dilute 200 µl of stock solution in 20 ml hexane p.a.
    Mix to homogenize
2. Perfume Extraction from Liquid Detergent without Perfume Microcapsules (Reference)
    Weigh 2 g of liquid detergent product into an extraction vessel
    Add 2 ml of Internal Standard Solution and close vessel
    Extract perfume by gently turning the extraction vessel upside-down for 20 times (manually)
    Add spoon tip of Sodium Sulphate
    After separation of layers, immediately transfer hexane-layer into Gas Chromatograph auto sampler-vial and cap vial
    Inject splitless (1.5 µl) into Gas Chromatograph injection-port
    Run Gas Chromatographic-Mass Spectrometric analysis
3. Perfume Extraction from Liquid Detergent with Perfume Microcapsules
    Weigh 2 g of liquid detergent product into an extraction vessel
    Add 2 ml of Internal Standard Solution and close vessel
    Extract perfume by gently turning the extraction vessel upside-down for 20 times (manually)
    Add spoon tip of Sodium Sulphate
    After separation of layers, immediately transfer hexane-layer into Gas Chromatograph auto sampler-vial and cap vial
    Inject splitless (1.5 µl) into Gas Chromatograph injection-port
    Run Gas Chromatographic-Mass Spectrometric analysis
4. Calculation
    The perfume leakage from capsules per individual Perfume Raw Material:
    % perfume leakage=((Area Perfume Raw Material caps×Area Internal Standard Solution ref×Weight ref)/(Area Internal Standard Solution caps×Area Perfume Raw Material ref×Weight caps))×100

(5) Odor Detection Threshold (ODT) is determined using a gas chromatograph. The gas chromatograph is calibrated to determine the exact volume of material injected by the syringe, the precise split ratio, and the hydrocarbon response using a hydrocarbon standard of known concentration and chain length distribution. The air flow rate is accurately measured and, assuming the duration of human inhalation to last 12 seconds, the sampled volume is calculated. Since the precise concentration at the detector at any point in time is known, the mass per volume inhaled is known, and hence the concentration of material. For example, to determinewhether a material has a threshold below 50 parts per bullion, solutions are delivered to the sniff port at the calculated concentration. A panelist sniffs the GC effluent and identifies the retention time when odor is noticed. The average among 6 panelists determines the threshold of noticeability. The necessary amount of analyte is injected into the column to achieve a 50 parts per billion concentration at the detector. Typical gas chromatograph parameters for determining odor detection thresholds are listed below:

GC: 5890 Series II with FID detector, 7673 Autosampler
Column: J&W Scientific DB-1
Length: 30 meters, 0.25 millimeter inside diameter, 1 micrometer film thickness
Method:
    split injection: 17/1 split ratio
    Autosampler: 1.13 microliters per injection
    Column flow: 1.10 milliLiters per minute
    Air Flow: 345 milliLiters per minute
    Inlet Temperature: 245 degrees Centigrade
    Detector Temperature: 285 degrees Centigrade
    Initial Temperature=50 degrees Centigrade, 5 degrees Centigrade per minute ramp rate, final temperature=280 degrees Centigrade, Final time=6 minutes
Leading assumptions: 12 seconds per sniff, GC air adds to sample dilution

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

PRM Synthesises

Synthesis Example for PRMs having Formula 1
A representative procedure is given for the synthesis of Table 1 Material 1.
A solution of n-butyllithium (2.2M in cyclohexane-70.5 mmol) is added drop wise to an ice cold solution of diisopropylamine (70.5 mmol) in 70 mL dry THF. After stirring for 10 minutes at this temperature, propionitrile (33.6 mmol) is added to the mixture. Prenyl bromide (67.1 mmol) is added after another mixing of 10 minutes at 0° C. Reaction conversion is followed by GC-MS and seen as complete after 15 minutes stirring at 0° C. The reaction is quenched by addition of a saturated $NH_4Cl$ aqueous solution and extracted with $Et_2O$. The combined organic layers are dried over $MgSO_4$ and concentrated under reduced pressure. The resulting oil is purified using a quick filtration over silica by elution with a petroleum ether-$Et_2O$ mixture (9-1). Concentration of the eluent under reduced pressure resulted in 2,5-dimethyl-2-(3-methylbut-2-enyl)hex-4-enenitrile as a colorless oil (97% yield-98% purity).

The obtained nitrile (32.4 mmol) is dissolved in dry $CH_2Cl_2$ (65 mL) at −60° C. At this temperature is added drop wise a diisobutylaluminiumhydride (42.0 mmol) solution (1.1 M cyclohexane). The resulting mixture is allowed to warm to ambient temperature for 3 hours. Reaction completion is observed by GC-MS. The mixture is cooled to 0° C. and a saturated aqueous sodium potassium tartrate solution is added carefully. This quenching is followed by stirring for 2 hours at ambient temperature. The resulting mixture is extracted with $CH_2Cl_2$, dried over $MgSO_4$ and reduced under reduced pressure to yield 2,5-dimethyl-2-(3-methylbut-2-enyl)hex-4-enal (93% yield-96% purity).

Synthesis Example for PRMs having Formula 2
A representative procedure is given for the synthesis of Table 1 Material 9.
A solution of n-butyllithium (2.2M in cyclohexane-19.7 mmol) is added drop wise to an ice cold solution of diisopropylamine (19.7 mmol) in 40 mL dry THF. After stirring for 10 minutes at this temperature, i-butyronitrile (18.8 mmol) is added to the mixture. 3-Bromocyclohex-1-ene (18.8 mmol) is added after another mixing of 10 minutes at 0° C. Reaction conversion is followed by GC-MS and seen as complete after 15 minutes stirring at 0° C. The reaction is quenched by addition of a saturated $NH_4Cl$ aqueous solution and extracted with $Et_2O$. The combined organic layers are dried over $MgSO_4$ and concentrated under reduced pressure. The resulting oil is purified using a quick filtration over silica by elution with a petroleum ether-$Et_2O$ mixture (9-1). Concentration of the eluent under reduced pressure resulted in 2-(cyclohex-2-enyl)-2-methylpropanenitrile as a colorless oil (95% yield-99% purity).

The obtained nitrile (18.6 mmol) is dissolved in dry $CH_2Cl_2$ (65 mL) at −60° C. At this temperature is added drop wise a diisobutylaluminiumhydride (24.2 mmol) solution (1.1 M cyclohexane). The resulting mixture is allowed to warm to ambient temperature for 3 hours. Reaction completion is observed by GC-MS. The mixture is cooled to 0° C. and a saturated aqueous sodium potassium tartrate solution is added carefully. This quenching is followed by stirring for 2 hours at ambient temperature. The resulting mixture is extracted with $CH_2Cl_2$, dried over $MgSO_4$ and concentrated under reduced pressure to yield 2-(cyclohex-2-enyl)-2-methylpropanal (90% yield-98% purity).

Synthesis Example for PRMs having Formula 3
A representative procedure is given for the synthesis of Table 1 Material 11.
A solution of n-butyllithium (2.2M in cyclohexane-31.5 mmol) is added drop wise to an ice cold solution of diisopropylamine (31.5 mmol) in 60 mL dry THF. After stirring for 10 minutes at this temperature, cyclopropanecarbonitrile (30.0 mmol) is added to the mixture. 3-Bromocyclohex-1-ene (30.0 mmol) is added after another mixing of 10 minutes at 0° C. Reaction conversion is followed by GC-MS and seen as complete after 15 minutes stirring at 0° C. The reaction is quenched by addition of a saturated $NH_4Cl$ aqueous solution and extracted with $Et_2O$. The combined organic layers are dried over $MgSO_4$ and concentrated under reduced pressure. The resulting oil is purified using a quick filtration over silica by elution with a petroleum ether-$Et_2O$ mixture (9-1). Concentration of the eluent under reduced pressure resulted in 1-(cyclohex-2-enyl)cyclopropanecarbonitrile as a colorless oil (97% yield-96% purity).

A iso-butyllithium solution (1.6 M-11.2 mmol) is added drop wise to a solution of the nitrile 1-(cyclohex-2-enyl) cyclopropanecarbonitrile (10.2 mmol) in 20 mL dry THF −20° C. After stirring for 15 minutes at −10/−20° C., full conversion is observed by GC-MS. The reaction is quenched with a H$_2$SO$_4$ solution (2M-20.4 mmol) and stirred at ambient temperature till full hydrolysis of the in situ formed imine is observed. The mixture is then extracted with Et$_2$O and washed with a saturated NaHCO$_3$ aqueous solution. The combined organic phases are dried over MgSO$_4$ and concentrated under reduced pressure. The resulting oil is purified using a quick filtration over silica gel by eluting with a petroleum ether-Et$_2$O mixture (9-1). Concentration of the eluent under reduced pressure resulted in 1-(1-(cyclohex-2-enyl)cyclopropyl)-3-methylbutan-1-one as a colorless oil (89% yield-97% purity).

Synthesis Example for PRMs having Formula 4

A representative procedure is given for the synthesis of Table 1 Material 16.

A solution of n-butyllithium (2.2M in cyclohexane-116.3 mmol) is added drop wise to an ice cold solution of diisopropylamine (116.3 mmol) in 220 mL dry THF. After stirring for 10 minutes at this temperature, cyclopropanecarbonitrile (110.8 mmol) is added to the mixture. Prenyl bromide (110.8 mmol) is added after another mixing of 10 minutes at 0° C. Reaction conversion is followed by GC-MS and seen as complete after 15 minutes stirring at 0° C. The reaction is quenched by addition of a saturated NH$_4$Cl aqueous solution and extracted with Et$_2$O. The combined organic layers are dried over MgSO$_4$ and concentrated under reduced pressure. The resulting oil is purified using a quick filtration over silica by elution with a petroleum ether-Et$_2$O mixture (9-1). Concentration of the eluent under reduced pressure resulted in 1-(3-methylbut-2-enyl)cyclopropanecarbonitrile as a colorless oil (95% yield-98% purity).

A methyllithium solution (1.6 M-30.5 mmol) is added drop wise to a solution of the nitrile 1-(3-methylbut-2-enyl)cyclopropanecarbonitrile (27.7 mmol) in 55 mL dry THF –20° C. After stirring for 15 minutes at –10/–20° C., full conversion is observed by GC-MS. The reaction is quenched with a H$_2$SO$_4$ solution (2M-55.5 mmol) and stirred at ambient temperature till full hydrolysis of the in situ formed imine is observed. The mixture is then extracted with Et$_2$O and washed with a saturated NaHCO$_3$ aqueous solution. The combined organic phases are dried over MgSO$_4$ and concentrated under reduced pressure. The resulting oil is purified using a quick filtration over silica gel by eluting with a petroleum ether-Et$_2$O mixture (9-1). Concentration of the eluent under reduced pressure resulted in 1-(1-(3-methylbut-2-enyl)cyclopropyl)ethanone as a colorless oil (89% yield-98% purity).

To a solution of the ketone 1-(1-(3-methylbut-2-enyl)cyclopropyl)ethanone (24.6 mmol) in 50 mL dry THF is added portion wise lithium-aluminiumhydride (7.4 mmol) at 0° C. Reaction completion is observed by GC-MS after 15 minutes of stirring at ambient temperature. The mixture is cooled to 0° C. and consequently is added: water (same amount of mL as mg hydride used), 15% NaOH solution (same amount of mL as mg hydride used) & water (2 times amount of mL as mg hydride used). This quenching is followed by stirring for 1 hour at ambient temperature. The resulting mixture is filtered over celite and the filter is washed with Et$_2$O. Concentration of the filtrate under reduced pressure resulted in 1-(1-(3-methylbut-2-enyl)cyclopropyl)ethanol as a colorless oil (100% yield-97% purity).

To a solution of the alcohol 1-(1-(3-methylbut-2-enyl)cyclopropyl)ethanol (5.1 mmol) in 15 mL dry THF is added sodium hydride (5.6 mmol) and iodomethane (7.6 mmol) at 0° C. The resulting mixture is allowed to stir at ambient temperature over night. The reaction is quenched with an aqueous saturated solution of ammonium chloride and subsequently extracted with Et$_2$O. The combined organic phases are dried over MgSO$_4$ and reduced under reduced pressure. The resulting oil is purified using a quick filtration over silica gel by eluting with a petroleum ether-Et$_2$O mixture (9-1). Concentration under reduced pressure resulted in 1-(1-methoxyethyl)-1-(3-methylbut-2-enyl)cyclopropane as a colorless oil (99% yield-99% purity).

Synthesis Example for PRMs having Formula 5

A representative procedure is given for the synthesis of Table 1 Material 21.

A solution of n-butyllithium (2.2M in cyclohexane-69.3 mmol) is added drop wise to an ice cold solution of diisopropylamine (69.3 mmol) in 130 mL dry THF. After stirring for 10 minutes at this temperature, i-butyronitrile (66.0 mmol) is added to the mixture. (Bromomethyl)cyclopropane (66.0 mmol) is added after another mixing of 10 minutes at 0° C. Reaction conversion is followed by GC-MS and seen as complete after 15 minutes stirring at 0° C. The reaction is quenched by addition of a saturated NH$_4$Cl aqueous solution and extracted with Et$_2$O. The combined organic layers are dried over MgSO$_4$ and concentrated under reduced pressure. The resulting oil is purified using a quick filtration over silica by elution with a petroleum ether-Et$_2$O mixture (9-1). Concentration of the eluent under reduced pressure resulted in 3-cyclopropyl-2,2-dimethylpropanenitrile as a colorless oil (96% yield-99% purity).

Synthesis Example for PRMs having Formula 6

A representative procedure is given for the synthesis of Table 1 Material 26.

A solution of n-butyllithium (2.2M in cyclohexane-63.0 mmol) is added drop wise to an ice cold solution of diisopropylamine (63.0 mmol) in 120 mL dry THF. After stirring for 10 minutes at this temperature, cyclobutanecarbonitrile (60.0 mmol) is added to the mixture. Prenyl bromide (60.0 mmol) is added after another mixing of 10 minutes at 0° C. Reaction conversion is followed by GC-MS and seen as complete after 15 minutes stirring at 0° C. The reaction is quenched by addition of a saturated NH$_4$Cl aqueous solution and extracted with Et$_2$O. The combined organic layers are dried over MgSO$_4$ and concentrated under reduced pressure. The resulting oil is purified using a quick filtration over silica by elution with a petroleum ether-Et$_2$O mixture (9-1). Concentration of the eluent under reduced pressure resulted in 1-(3-methylbut-2-enyl)cyclobutanecarbonitrile as a colorless oil (95% yield-97% purity).

Some of the obtained nitrile 1-(3-methylbut-2-enyl)cyclobutanecarbonitrile (13.4 mmol) is dissolved in dry CH$_2$Cl$_2$ (30 mL) at –60° C. At this temperature is added drop wise a diisobutylaluminiumhydride (14.7 mmol) solution (1 M cyclohexane). The resulting mixture is allowed to warm to ambient temperature for 3 hours. Reaction completion is observed by GC-MS. The mixture is cooled to 0° C. and a saturated aqueous sodium potassium tartrate solution is added carefully. This quenching is followed by stirring for 2 hours at ambient temperature. The resulting mixture is extracted with CH$_2$Cl$_2$, dried over MgSO$_4$ and reduced under reduced pressure to yield 1-(3-methylbut-2-enyl)cyclobutanecarbaldehyde (99% yield-97% purity).

Synthesis Example for PRMs having Formula 7

A representative procedure is given for the synthesis of Table 1 Material 27.

A solution of n-butyllithium (2.2M in cyclohexane-18.5 mmol) is added drop wise to an ice cold solution of diisopropylamine (18.5 mmol) in 35 mL dry THF. After stirring for 10 minutes at this temperature, i-butyronitrile (17.6 mmol) is added to the mixture. (1R,5S)-2-(Chloromethyl)-6,6-dimethylbicyclo[3.1.1]hept-2-ene (17.6 mmol) is added after another mixing of 10 minutes at 0° C. Reaction conversion is followed by GC-MS and seen as complete after 15 minutes stirring at 0° C. The reaction is quenched by addition of a saturated NH$_4$Cl aqueous solution and extracted with Et$_2$O. The combined organic layers are dried over MgSO$_4$ and concentrated under reduced pressure. The resulting oil is purified using a quick filtration over silica by elution with a petroleum ether-Et$_2$O mixture (9-1). Concentration of the eluent under reduced pressure resulted in 3-((1R,5S)-6,6-Dimethylbicyclo[3.1.1]hept-2-en-2-yl)-2,2-dimethylpropanenitrile as a colorless oil (86% yield-99% purity).

Example 2

Preformed Amine Reaction Product

The following ingredients are weighted off in a glass vial:
50% of the perfume material comprising one or more Table 1 PRMs
50% of Lupasol WF (CAS#09002-98-6) from BASF, is put at 60° C. in warm water bath for 1 hour before use. Mixing of the two ingredients is done by using the Ultra-Turrax T25 Basic equipment (from IKA) during 5 minutes. When the mixing is finished the sample is put in a warm water bath at 60° C. for ±12 hours. A homogenous, viscous material is obtained. In the same way as described above different ratios between the components can be used:

| | Weight % | | | | |
|---|---|---|---|---|---|
| Perfume Material | 40 | 50 | 60 | 70 | 80 |
| Lupasol WF | 60 | 50 | 40 | 30 | 20 |

Example 3

84 wt % Core/16 wt % Wall Melamine Formaldehyde (MF) Capsule (PAD Reservoir System 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil comprising one or more Table 1 PRMs is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 4

Process of Making a Polymer Assisted Delivery (PAD) Matrix System

A mixture comprising 50% of a perfume composition comprising one or more Table 1 PRMs, 40% of carboxyl-terminated Hycar®1300X18 (CAS#0068891-50-9) from Noveon, (put at 60° C. in warm water bath for 1 hour before mixing) and 10% of Lupasol® WF(CAS#09002-98-6) from BASF (put at 60° C. in warm water bath for 1 hour before mixing). Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

In the same way as described above different ratios between the components can be used:

| | Weight % | | | | |
|---|---|---|---|---|---|
| Perfume composition | 40 | 50 | 60 | 70 | 80 |
| Lupasol ® WF | 12 | 10 | 8 | 6 | 4 |
| Hycar ® CTBN1300X18 | 48 | 40 | 32 | 24 | 16 |

| | Weight % | | | | | | | |
|---|---|---|---|---|---|---|---|---|
| Perfume composition | 50 | 50 | 50 | 50 | 50 | 50 | 50 | 50 |
| Lupasol ® WF | 2.5 | 5 | 7.5 | 10 | 12.5 | 15 | 17.5 | 20 |
| Hycar ® CTBN 1300X18 | 47.5 | 45 | 42.5 | 40 | 37.5 | 35 | 32.5 | 30 |

Example 5

Product Formulation

Non-limiting examples of product formulations containing PRMs disclosed in the present specification perfume and amines summarized in the following table.

| (% wt) | EXAMPLES | | | | | | | | | |
|---|---|---|---|---|---|---|---|---|---|---|
| | XI | XII | XIII | XIV | XV | XVI | XVII | XVIII | XIX | XX |
| FSA $^a$ | 14 | 16.47 | 14 | 12 | 12 | 16.47 | — | — | 5 | 5 |
| FSA $^b$ | | | | | — | | 3.00 | — | — | — |
| FSA $^c$ | | | | | — | | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch $^d$ | 1.25 | 1.47 | 2.00 | 1.25 | — | 2.30 | 0.5 | 0.70 | 0.71 | 0.42 |
| Amine * | 0.6 | 0.75 | 0.6 | 0.75 | 0.37 | 0.60 | 0.37 | 0.6 | 0.37 | 0.37 |
| Perfume X $^e$ | 0.40 | 0.13 | 0.065 | 0.25 | 0.03 | 0.030 | 0.030 | 0.065 | 0.03 | 0.03 |
| Phase | 0.21 | 0.25 | 0.21 | 0.21 | 0.14 | — | — | 0.14 | — | — |

| (% wt) | XI | XII | XIII | XIV | XV | XVI | XVII | XVIII | XIX | XX |
|---|---|---|---|---|---|---|---|---|---|---|
| Stabilizing Polymer [f] | — | — | — | — | — | — | — | — | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Additional Neat Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[e] Perfume comprising one or more Table 1 PRMs.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculan 44.
* One or more materials comprising an amine moiety as disclosed in the present specification.
† balance

Example 6

Dry Laundry Formulations

| Component | % w/w granular laundry detergent composition | | | | | | |
|---|---|---|---|---|---|---|---|
| | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |

-continued

| Component | % w/w granular laundry detergent composition | | | | | | |
|---|---|---|---|---|---|---|---|
| | A | B | C | D | E | F | G |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Additional Neat Perfume** | 0.5 | 0.5 | 0.5 | 0.5 | 0.5 | 0.5 | 0.5 |
| Amine* | 0.1 | 0.5 | 0.0 | 0.01 | 0.02 | 0.00 | 0.07 |
| Perfume Delivery System As Disclosed In The Present Specification Including Examples 2-4 | 0.05 | 0.0 | 0.1 | 0.0 | 0.2 | 0.4 | 0.0 |
| Perfume comprising one or more PRMs from Table 1 | 0.3 | 0.4 | 0.01 | 0.02 | 0.04 | 0.1 | 0.1 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*One or more materials comprising an amine moiety as disclosed in the present specification.
**Optional Example 7

Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Additional Neat Perfume** | 0.7 | 0.5 | 0.8 | 0.8 | 0.6 | 0.6 |
| Amine* | 0.01 | 0.10 | 0.0 | 0.10 | 0.20 | 0.05 |
| Perfume comprising one or more PRMs from Table 1 | 0.02 | 0.15 | 0.0 | 0.2 | 0.3 | 0.1 |

-continued

| Ingredient | HDL 1 | HDL 2 | HDL3 | HDL4 | HDL 5 | HDL 6 |
|---|---|---|---|---|---|---|
| Perfume Delivery System As Disclosed In The Present Specification Including Examples 2-4 | 0.2 | 0.02 | 0.4 | 0.0 | 0.0 | 0.0 |
| Water | Balance | Balance | Balance | Balance | Balance | Balance |

*One or more materials comprising an amine moiety as disclosed in the present specification.
**Optional.

Example 8

Shampoo Formulation

| Ingredient | |
|---|---|
| Ammonium Laureth Sulfate (AE$_3$S) | 6.00 |
| Ammonium Lauryl Sulfate (ALS) | 10.00 |
| Laureth-4 Alcohol | 0.90 |
| Trihydroxystearin[7] | 0.10 |
| Perfume comprising one or more PRMs from Table 1 | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone[9,10,11] | 1.00[9] |
| Water and Minors (QS to 100%) | Balance |

Example 9

Fine Fragrance Formulation

| Ingredient | 1 | 2 | 3 |
|---|---|---|---|
| Cyclic oligosaccharide | 0 | 5 | 10 |
| Ethanol | 90 | 75 | 80 |
| Perfume comprising one or more PRMs from Table 1 | 10 | 20 | 10 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A perfume comprising an optional solvent and a perfume raw material selected from the group consisting of:
    a) a perfume raw material having the following structure:

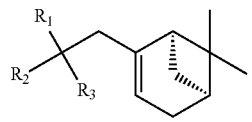

wherein $R_1$ is selected from the group consisting of:
   (i) a nitrile moiety;
   (ii) $COR_4$
   wherein $R_4$ is selected from the group consisting of a straight or branched $C_1$-$C_6$ alkyl moiety; a straight or branched $C_2$-$C_6$ alkenyl moiety; a straight or branched $C_2$-$C_6$ alkyne moiety; a non-substituted phenyl moiety; a substituted phenyl moiety, in one aspect, said substituted phenyl moiety may comprise a substituent selected from methyl and/or ethyl;
   (iii) $CR_5R_6OR_7$ wherein $R_5$, $R_6$ and $R_7$ are each independently selected from a group consisting of hydrogen, a straight or branched $C_1$-$C_5$ alkyl moiety, a straight or branched $C_2$-$C_5$ alkenyl moiety, a straight or branched $C_2$-$C_5$ alkyl moiety comprising a ketone moiety, and a straight or branched $C_2$-$C_5$ alkenyl moiety comprising a ketone moiety;
   (iv) $COOR_8$ where $R_8$ is selected from a group consisting of a straight or branched $C_1$-$C_5$ alkyl moiety, a straight or branched $C_2$-$C_5$ alkenylmoiety;
wherein $R_2$ is selected from the group consisting of:
   (i) a straight or branched $C_3$-$C_6$ alkyl moiety;
   (ii) a straight or branched $C_2$-$C_6$ alkenyl moiety;
   (iii) a straight or branched $C_2$-$C_6$ alkyne moiety; and
   (iv) $CH_2$-cyclopropyl
wherein $R_3$ is selected from the group consisting of:
   (i) a straight or branched $C_3$-$C_6$ alkyl moiety;
   (ii) a straight or branched $C_2$-$C_6$ alkenyl moiety;
   (iii) a straight or branched $C_2$-$C_6$ alkyne moiety; and
when $R_2$ and $R_3$ are taken together, $R_2$ and $R_3$ form a ring structure;
with the proviso that the perfume raw material is not 3-((1R,5S)-6,6-dimethylbicyclo[3.1.1]hept-2-en-2-yl)-2,2-dimethylpropanal.

2. A perfume according to claim 1 comprising, based on total perfume weight, from about 0.0001% to about 50% of said perfume raw material.

3. A consumer product comprising the perfume according to claim 2, said consumer product being a cleaning and/or treatment composition and comprising an adjunct ingredient.

4. A consumer product according to claim 3, said consumer product being a fabric and/or hard surface cleaning and/or treatment composition, said composition comprising, based on total composition weight, from about 0.00001% to about 35% of said perfume.

5. A consumer product according to claim 3, said consumer product being a detergent, said detergent comprising, based on total detergent weight, from about 0.00001% to about 35% of said perfume.

6. A consumer product according to claim 3, said consumer product being a highly compacted consumer product, said highly compacted consumer product comprising, based on total highly compacted consumer product weight, from about 0.00001% to about 35% of said perfume.

7. A consumer product comprising the perfume according to claim 1 and an adjunct ingredient.

8. A perfume delivery system comprising, based on total delivery system weight, from about 0.001% to about 99% of the perfume of claim 1, said perfume delivery system being a polymer assisted delivery system; a molecule-assisted delivery system; a fiber-assisted delivery system; an amine assisted delivery system; a cyclodextrin delivery system; a starch encapsulated accord; an inorganic carrier delivery system; or a pro-perfume.

9. A perfume delivery system according to claim 8, said perfume delivery system being a nanocapsule or a microcapsule comprising, based on total nanocapsule or microcapsule weight, from about 0.001% to about 99% of said perfume.

10. A perfume delivery system according to claim 9, said perfume delivery system being a starch encapsulated accord.

11. A perfume delivery system according to claim 9, said perfume delivery system being a cyclodextrin delivery system that comprises, based on total perfume delivery system weight, from about 2% to about 20% of said perfume.

12. A perfume delivery system according to claim 9, said perfume delivery system being a polymer assisted delivery matrix system.

13. A perfume delivery system according to claim 9, said perfume delivery system being an amine assisted delivery system.

14. A perfume delivery system according to claim 9, said perfume delivery system being a pro-perfume amine reaction product.

15. A consumer product comprising, based on total consumer product weight, from about 0.001% to about 20% of the perfume delivery system of claim 9.

* * * * *